United States Patent [19]

Imazaki et al.

[11] 4,301,173
[45] Nov. 17, 1981

[54] HORTICULTURAL COMPOSITION AND METHOD FOR CONTROLLING PLANT MITES

[75] Inventors: Hideyuki Imazaki, Osaka; Masazumi Fujikawa, Takatsuki; Hiromitsu Kariya, Higashimurayama, all of Japan

[73] Assignees: Nitto Kasei Co., Ltd., Osaka; Kanesho Co., Ltd., Tokyo, both of Japan

[21] Appl. No.: 125,278

[22] Filed: Feb. 27, 1980

[30] Foreign Application Priority Data

Mar. 2, 1979 [JP] Japan .................................. 54-24753

[51] Int. Cl.³ .............................................. A61K 31/32
[52] U.S. Cl. .................................. 424/288; 260/429.7
[58] Field of Search ......................................... 424/288

[56] References Cited

U.S. PATENT DOCUMENTS

| | | | |
|---|---|---|---|
| 3,539,289 | 11/1970 | Suzuki et al. | 424/288 X |
| 3,876,795 | 4/1975 | Cracco et al. | 424/288 |
| 4,153,574 | 5/1979 | Beiter et al. | 424/288 X |

FOREIGN PATENT DOCUMENTS

| | | |
|---|---|---|
| 53-23684 | of 1978 | Japan . |
| 53-29988 | of 1978 | Japan . |
| 53-108930 | of 1978 | Japan . |
| 53-121723 | of 1978 | Japan . |
| 54-2250 | of 1979 | Japan . |

Primary Examiner—Frank Cacciapaglia, Jr.

[57] ABSTRACT

An agricultural or horticultural miticidal composition for controlling mites which cause damage to plants, said miticidal composition comprising
 (1) a liquid carrier and/or a solid carrier, and
 (2) as an active ingredient, a trialkyltin compound of the formula

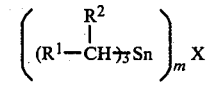

wherein $R^1$ represents a linear alkyl group having 6 to 11 carbon atoms, $R^2$ represents a hydrogen atom or a methyl group, the total number of carbon atoms of $R^1$ and $R^2$ is from 7 to 11, m is an integer of 1 or 2, and X represents a chlorine atom, a bromine atom, a fluorine atom, a hydroxyl group, an acyloxy group, a dithiocarbamate group or a group of the formula $-SR^3$, in which $R^3$ represents an alkyl group having 1 to 12 carbon atoms or an aryl group, when m is 1, and a member selected from the class consisting of an oxygen atom, a sulfur atom and a sulfuric acid group when m is 2; and a method for controlling mites using the same.

12 Claims, No Drawings

HORTICULTURAL COMPOSITION AND METHOD FOR CONTROLLING PLANT MITES

Mites parasitic on plants pose a great problem because they do enormous damage to agricultural and horticultural crops and plants. They have a high reproductive power, and under certain environmental conditions, may grow rapidly within short periods of time. Moreover, since they easily gain resistance to chemicals, new controlling agents must always be developed to cope with the problem.

Previously, linear and branched tri-(lower alkyl)tin compounds have been known to exhibit superior biological activities and have been used for controlling noxious organisms such as insects, mites, bacteria, and fungi. For example, Japanese Patent Publication No. 2250/79 discloses a miticidal concentrate containing a compound of the formula $(R_3Sn)_2O$ wherein R is an acyclic alkyl group having 5 to 7 carbon atoms. Japanese Laid-Open Patent Publication No. 108930/78 describes a pest controlling composition comprising a compound resulting from the attaching to a tin atom of three groups of the formula

wherein each of $R^1$ and $R^2$ represents a linear or branched alkyl group having 1 to 4 carbon atoms, the total number of carbon atoms of $R^1$ and $R^2$ being 5 to 7. Furthermore, Japanese Laid-Open Patent Publication No. 121723/78 discloses a fungicidal, insecticidal and miticidal composition comprising a compound resulting from the attaching to a tin atom of three groups of the formula

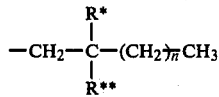

wherein R* represents a methyl or ethyl group, R** represents a hydrogen atom or a methyl or ethyl group, and n is 0, 1 or 2, the total number of carbon atoms of this group being 6 to 9.

In the three inventions cited above, the organic groups bonded to tin are linear alkyl groups having 5 to 7 carbon atoms or branched alkyl groups whose longest chain has 4 to 5 carbon atoms. Tri-organotin compounds comprising these groups ar toxic to plants, and when applied to crops and horticultural plants in the young seedling stage or the new leaf developing stage or after growth, may markedly damage certain kinds of these plants. Hence, they are not entirely satisfactory in providing miticidal agents of practical value. These compounds also have the defect of causing death to those mites which prey on various noxious mites on plants, or to other beneficial organisms. The various defects of these known compounds are given hereinbelow as comparisons.

Other various tri-organotin compounds or organic compounds have been used as miticides, but many of them exhibit different activities against different mites parasitic on plants. For example, it is frequently seen that a miticide effective against *Panonychus ulmi* Koch parasitic on apple trees is ineffective against *Tetranychus urticae* Koch which is also parasitic on apple trees.

Accordingly, ideal miticidal compositions should not cause any phytotoxicity to agricultural crops and horticultural plants, should be effective against a broad range of mites noxious to the plants, and should not adversely affect beneficial insects or predator mites which prey on noxious mites.

Extensive investigations of the present inventors have unexpectedly led to the discovery that trialkyltin compounds having at least 8 carbon atoms previously considered to have extremely low biological activities possess miticidal activities which meet the aforesaid requirements of ideal miticidal compositions.

According to this invention, there is provided an agricultural or horticultural miticidal composition for controlling mites which cause damage to plants, said miticidal composition comprising (1) a liquid carrier and/or a solid carrier, and (2) as an active ingredient, a trialkyltin compound of the formula

wherein $R^1$ represents a linear alkyl group having 6 to 11 carbon atoms, $R^2$ represents a hydrogen atom or a methyl group, the total number of carbon atoms of $R^1$ and $R^2$ is from 7 to 11, m is an integer of 1 or 2, and X represents a chlorine atom, a bromine atom, a fluorine atom, a hydroxyl group, an acyloxy group, a dithiocarbamate group or a group of the formula $-SR^3$, in which $R^3$ represents an alkyl group having 1 to 12 carbon atoms or an aryl group, when m is 1, and a member selected from the class consisting of an oxygen atom, a sulfur atom and a sulfuric acid group when m is 2.

Trialkyltin compounds of general formula [I] in which $R^2$ is hydrogen are known, and are usually synthesized by subjecting a tetraalkyltin and tin tetrachloride to a re-distribution reaction to form a trialkyltin chloride, and substituting the desired group for chlorine to form the corresponding derivative. When $R^2$ is a methyl group or $R^1$ has 11 carbon atoms, the trialkyltin compound can be synthesized by the following procedure.

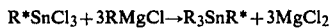

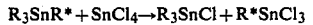

In the above formulae, R represents the group

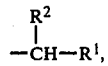

and R* represents a lower alkyl group containing 1 to 4 carbon atoms. The resulting trialkyltin chloride is converted to the desired final compound.

The group

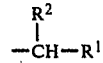

in general formula [I] is, for example, n-octyl, 2-octyl (i.e., 1-methylheptyl), n-nonyl, 2-nonyl, n-decyl, 2- decyl, n-undecyl, 2-undecyl, n-dodecyl, 2-dodecyl, etc. depending upon the position at which the group is bonded to tin. Especially preferred are n-octyl, 2-octyl, and n-dodecyl groups. Thus, examples of the trialkyltin compound used as an active ingredient in the composition of this invention include tri-n-octyltin chloride, tri-n-octyltin bromide, tri-n-octyltin fluoride, tri-n-octyltin acetate, tri-n-octyltin hydroxide, bis(tri-n-octyltin)oxide, tri-n-octyltin N,N-dimethyldithiocarbamate, tri-n-octyltin lauryl mercaptide, bis(tri-n-octyltin) sulfide, bis(tri-n-octyltin) sulfate, tri-2-octyltin chloride, tri-2-ocltyltin fluoride, bis(tri-2-octyltin) oxide, tri-2-octyltin N,N-dimethyldithiocarbamate, tri-2-octyltin butylmercaptide, bis(tri-2-octyltin) sulfide, tri-n-decyltin chloride, tri-2-decyltin fluoride, bis(tri-n-decyltin) oxide, tri-n-dodecyltin chloride, bis(tri-n-dodecyltin) oxide, tri-n-dodecyltin hydroxide, tri-n-dodecyltin fluoride, tri-n-dodecyltin N,N-dimethyldithiocarbamate, and bis(tri-2-dodecyltin) sulfide. Of these, tri-n-octyltin chloride, bis(tri-n-octyltin) oxide, tri-2-octyltin chloride, bis(tri-2-octyltin) oxide, tri-n-dodecyltin chloride, and tri-n-dodecyltin hydroxide are especially preferred.

The trialkyltin compound, the active ingredient of the composition of this invention, shows superior controlling effects against a broad range of mites which are parasitic on various plants and cause damage thereto. Examples of these mites are mites which are parasitic mainly on fruit trees, such as *Panonychus citri* McGregor, *Panonychus ulmi* Koch, *Tetranychus urticae* Koch, *Eotetranychus sexamaculatus* Riley, *Aculops pelekassi* Keifer, *Calepitrimerus vitis* Nalepa, *Brevipalpus lewisi* McGregor, *Tetranychus viennensis* Zacker, and *Tenuipalpus zhizhilashuilial* Reck; mites parasitic mainly on specialty crops (tea, mulberry, etc.) such as Tetranychus Kanzawai Kishida, *Tetranychus truncatus* Ehara, and *Brevipalpus obovatus* Donnadieu; mites parasitic mainly on vegetables and petals, such as *Tetranychus telarius* Linné, *Tetranychus desertorus* Banks, *Tetranychus urticae* Koch, and Tetranychus Kanzawai Kishida; and mites parasitic on forest trees, such as *Oligohychus nondoensis* Ehara and *Eotetranychus suginamensis* Yokoyama.

On the other hand, these trialkyltin compounds are not toxic to predator mites, which prey on the aforesaid noxious mites and do not damage plants, such as *Amblyseius longispinosus* Evans and *Typhlodromus vulgaris* Ehara of Family Phytoseiidae, and mites of Family Stimaeidae or Anystidae, and beneficial insects as mites predators such as *Stethorus japonicus* Kamiya and *Orius sauteri* Poppius.

The miticidal composition of this invention does not cause phytotoxicity to most plants including cotton, grape, pear, apple, citrus fruits, tea, carnation, eggplant, kidney bean, radish, etc.

The composition of this invention may be used in various formulations such as wettable powders, emulsifiable concentrates, dusts and flowable preparations by mixing the active ingredient of general formula [I] with at least one conventional agriculturally acceptable additive or assistant in accordance with an ordinary method of formulating agricultural chemicals. The aforesaid additives or assistants include organic solvents, water and other liquid carriers, surface active agents, and granular or particulate solid carriers.

In formulating the active ingredient in accordance with this invention into a solid or a particulate solid composition, it is mixed with a conventional fine solid carrier such as clay, talc, white carbon (silica), diatomaceous earth, bentonite, fuller's earth, attapulgite, pyrophyllite, vermiculite, kaolin, chaulk, gypsum, and wood flour. The dust composition may be used as a concentrate, and then mixed with an additional carrier in order to obtain the desired amount of the active ingredient in the composition of this invention for use in controlling mites.

If desired, the solid composition may be mixed with a surface active agent or a dispersing agent in order to obtain a wettable powder. This powder can be easily dispersed in a liquid carrier to give a spray liquid or dispersion. Suitable surface active agents or dispersing agents include ionic or nonionic emulsifiers or dispersing agents such as higher alkoxysulfonates, polyoxyethylene sorbitan, alkylphenoxy polyethoxy ethanols, lignosulfonates, alkylaryl sulfonates, complex ether/alcohol, and mahogany soaps. If further desired, they may also include wetting agents and protective colloids. To use such wettable powders, they may be diluted with water or a water-oil mixture.

The active ingredient of this invention may also be prepared as an emulsifiable concentrate or a water-dispersible liquid composition. In this case, the active ingredient may be mixed with a suitable liquid carrier and a suitable surface active agent in order to prepare an emulsifiable concentrate. Examples of the liquid carrier are water, methanol, ethanol, isopropanol, methyl ethyl ketone, acetone, methylene chloride, benzene, toluene, xylene, n-heptane, and petroleum distillates.

To apply the emulsifiable concentrate, it is further diluted with water to prepare a spray liquid or a solution in which the active ingredient is uniformly suspended or dissolved. Surfactants or dispersing agents for use in preparing such an emulsifiable concentrate may be those exemplified hereinabove. Typical examples are alkylphenoxy polyethoxyethanols and lignosulfonates. These surfactants or dispersing agents are used generally in an amount within the range of about 0.5 to about 10% by weight based on the weight of the concentrate.

Usually, the amount of the active ingredient in the composition is about 1 to about 80% by weight based on the total weight of the composition whether the composition is in the form of a solid or a fine solid or an emulsifiable concentrate.

The miticidal composition of this invention may be used in combination with other miticidal agents, insecticides, fungicides, plant growth regulators, fertilizers, etc.

In application to plants, the composition generally contains about 20 to about 60,000 ppm of the organotin compound of formula [I] per hectare depending upon the amount of the composition applied. When an ordinary technique of applying a diluent is used, the concentration of the organotin compound in the composition is generally about 50 to about 3,000 ppm, preferably about 125 to about 1,500 ppm. When the composition is to be applied by using low volume (LV) and ultralow volume (ULV) techniques which have recently gained wide acceptance, the concentration of the organotin compound in the composition is generally 1,200 to 36,000 ppm, preferably about 2,400 to about 30,000 ppm.

Whichever technique may be used for application, the amount of the organotin compound to be applied is desirably about 0.09 to about 3.5 kg, preferably about 0.22 to about 2.3 kg, per hectare depending upon the type of the crop to be treated, the degree of growing of the leaves, and the degree of damage done by mites. For convenience of handling large quantities, the composition is generally prepared as a concentrate which can be diluted to the desired concentration with water, a solvent or another inert carrier just prior to application.

The miticidal composition of this invention comprising the trialkyltin compound of formula [I] as an active ingredient exhibits a marked controlling activity on a broad range of noxious mites without affecting predators of the mites and causing phytotoxicity to plants. This is quite unexpected in view of the fact that trialkyltin compounds having at least 8 carbon atoms have been considered to possess very low biological activities.

While the present invention has been described hereinabove with reference to specific embodiments, the invention is not to be limited thereby but modifications are possible within the spirit and scope of the invention as defined in the appended claims.

Preparation Examples, Examples, and Test Examples are shown below. In these examples, all parts and percentages are by weight.

PREPARATION EXAMPLE 1

A 1-liter four-necked flask equipped with a thermometer, a condenser, a stirrer and a dropping funnel was charged with 19.4 g (0.8 mole) of magnesium, 118.9 g (0.8 mole) of 2-chlorooctane and 200 g of tetrahydrofuran, and they were reacted in a stream of nitrogen. To the resulting 2-octyl magnesium chloride solution was added dropwise a solution of 67.7 g (0.24 mole) of mono-n-butyltin trichloride in 200 ml of xylene with stirring at room temperature over the course of 30 minutes. The reaction mixture was reacted for 3 hours at the refluxing temperature, and then subjected to hydrolysis to obtain 120 g of n-butyl tri-2-octyltin having a purity of 98.7%.

The same 500 ml four-necked flask as used above was charged with 115 g of n-butyl tri-2-octyltin, 57.3 g of tin tetrachloride and 200 ml of n-heptane, and they were reacted at 40° to 50° C. for 1 hour. After the reaction, the reaction mixture was washed three times with 100 ml of 10% hydrochloric acid solution, and then the by-product mono-n-butyltin trichloride was removed. The organic layer was dried over anhydrous magnesium sulfate, and concentrated to obtain 105 g of liquid tri-2-octyltin chloride having a purity of 96.1%.

Furthermore, tri-2-octyltin chloride was treated respectively with an aqueous solution of sodium fluoride and an aqueous solution of sodium hydroxide to obtain waxy tri-2-octyltin fluoride and liquid bis(tri-2-octyltin) oxide, respectively.

PREPARATION EXAMPLE 2

The same reactor as used in Preparation Example 1 was charged with 12.1 g (0.5 mole) of magnesium, 102.4 g (0.5 mole) of n-dodecyl chloride and 200 g of tetrahydrofuran, and they were reacted in a stream of nitrogen. To the resulting n-dodecyl magnesium chloride solution was added dropwise a solution of 42.3 g (0.15 mole) of mono-n-butyltin trichloride in 200 ml of xylene with stirring at room temperature over the course of 30 minutes. Then, the reaction mixture was reacted for 3 hours at the refluxing temperature, and then subjected to a hydrolysis treatment to obtain 99.8 g of n-butyl tri-n-dodecyltin having a purity of 98.7% as an oily substance.

A 500 ml four-necked flask was charged with 95.0 g of n-butyl tri-n-dodecyltin, 36.4 g of tin tetrachloride and 150 ml of n-heptane, and they were reacted at 40° to 50° C. for 1 hour. After the reaction, the reaction mixture was washed three times with 100 ml of 10% aqueous solution of hydrochloric acid to remove mono-n-butyltin trichloride. The organic layer was dried with anhydrous magnesium sulfate, and concentrated to afford 89.3 g of tri-n-dodecyltin chloride having a purity of 97.2% as an oily substance (m.p. 30° to 32° C.).

The tri-n-dodecyltin chloride was treated with a 20% aqueous methanol solution of sodium hydroxide to afford tri-n-dodecyltin hydroxide having a melting point of 58° to 61° C.

EXAMPLE 1

Twenty parts of each of the compounds listed below, 70 parts of clay, 5 parts of white carbon, 3 parts of lignin sulfonate (Sanekis P-201, a trademark) and 2 parts of a higher alcohol sulfate ester salt (New Kalgen 204, a trademark) were uniformly mixed, and finely pulverized to form 100 parts of a wettable powder.

| Number | Compounds of the invention (active ingredient) | Property |
|---|---|---|
| I | Tri-n-octyltin fluoride | m.p. 189–192° C. |
| II | Tri-2-octyltin fluoride | waxy |
| III | Tri-n-dodecyltin hydroxide | m.p. 58–61° C. |

EXAMPLE 2

Twenty parts of each of the compounds listed below, 73 parts of xylene, a mixture of 3 parts of polyoxy ethylene alkyl ether and 2 parts of polyoxyethylene alkylaryl ester (Toxnul 500, a trademark) and 2 parts of calcium dodecylbenzenesulfonate were uniformly mixed with stirring to afford 100 parts of an emulsifiable concentrate.

| Number | Compound of this invention (active ingredient) | Property |
|---|---|---|
| IV | Bis(tri-n octyltin) oxide | $n_D^{30} = 1.4773$ |
| V | Tri-n octyltin lauryl mercaptide | $n_D^{30} = 1.4822$ |
| VI | Bis(tri-2-octyltin) oxide | $n_D^{30} = 1.4850$ |
| VII | Tri-n-decyltin chloride | $n_D^{30} = 1.4760$ |
| VIII | Tri-n-dodecyltin chloride | m.p. 30–32° C. |
| IX | Tri-n-octyltin chloride | $n_D^{30} = 1.4779$ |
| X | Tri-n-octyltin N,N dimethyl-thiocarbamate | $n_D^{30} = 1.5157$ |
| XI | Tri-n-octyltin acetate | m.p. 46–48° C. |

TEST EXAMPLE 1

The wettable powders and emulsifiable concentrates obtained in Examples 1 and 2 were diluted to predetermined concentrations, and sprayed onto 15-year old mandarin orange trees (variety Unshu), and the population of *Panonychus citri* McGregor before and after spraying was examined. As control chemicals, bis(tri-n-pentyltin) oxide, tricyclohexyltin hydroxide, bis(tri-n-heptyltin) oxide and tri(2,2-dimethylbuthyltin) chloride were formulated in the same way as above to form chemicals of the predetermined concentrations. They were also sprayed, and their effects were determined.

The mite population represents the average number of adult mites per 50 leaves in three replicates. Each chemical was sprayed by a powdered sprayer at a rate of about 600 liters per 10 ares so that it was fully applied to the entire trees. The phytotoxicity was examined by the naked eye on a scale of four grades ranging from (—) which represent no injury to (+ + +) which represents enormous injury.

The results are shown in Table 1.

In the table, the concentration (ppm) of the active ingredient means the concentration of the compound of this invention in the final form of a miticidal composition prepared for spraying by diluting each of the wettable powders and emulsifiable concentrates shown in Examples 1 and 2 with water. The same is true for the other tables.

TABLE 1

| Compound No. | Concentration of the active ingredient (ppm) | Number of mites before spraying | Number of mites counted 30 days after spraying | Phytotoxicity |
|---|---|---|---|---|
| I | 250 | 432 | 0 | — |
| II | 250 | 407 | 0 | — |
| III | 125 | 386 | 0 | — |
| IV | 125 | 436 | 0 | — |
| V | 250 | 415 | 0 | — |
| VI | 125 | 423 | 0 | — |
| VII | 250 | 419 | 0 | — |
| VIII | 250 | 397 | 0 | — |
| IX | 125 | 397 | 0 | + |
| X | 250 | 413 | 0 | — |
| XI | 250 | 402 | 0 | — |
| Comparison A | 125 | 410 | 0 | + + |
| Comparison B | 125 | 421 | 0 | + |
| Comparison D | 125 | 396 | 0 | + + |
| Comparison E | 125 | 411 | 0 | + + |
| Not sprayed | — | 382 | 635 | — |

Note
Comparison A: bis(tri-n-pentyltin) oxide
Comparison B: tricyclohexyltin hydroxide
Comparison D: bis(tri-n-heptyltin) oxide
Comparison E: tri(2,2-dimethylbutyltin) chloride

TEST EXAMPLE 2

Each of the wettable powders and emulsifiable concentrates obtained in Examples 1 and 2 were diluted to predetermined concentrations, and were sprayed onto 10-year old apple tree (variety Orei). The populations of *Panonychus ulmi* Koch and *Tetranychus urticae* Koch were examined before and after spraying, and the effects of the miticidal compositions were determined.

The method of examining the mite populations, the method of spraying the chemicals and the evaluation of phytotoxicity were the same as in Test Example 1. The results are shown in Table 2.

TABLE 2

| Compound No. | Concentration of the active ingredient (ppm) | Number of mites (*Panonychus ulmi* Koch) | | Number of mites (*Tetranychus urticae* Koch) | | Phytotoxicity |
|---|---|---|---|---|---|---|
| | | Before spraying | 30 days after spraying | Before spraying | 30 days after spraying | |
| I | 500 | 200 | 0 | 210 | 0 | — |
| | 250 | 211 | 105 | 209 | 113 | — |
| II | 500 | 203 | 0 | 216 | 0 | — |
| | 250 | 197 | 25 | 193 | 37 | — |
| III | 250 | 214 | 0 | 201 | 0 | — |
| | 125 | 195 | 0 | 196 | 0 | — |
| IV | 250 | 201 | 0 | 204 | 0 | — |
| | 125 | 208 | 0 | 196 | 0 | — |
| VI | 250 | 206 | 0 | 191 | 0 | — |
| | 125 | 213 | 0 | 205 | 0 | — |
| VII | 250 | 231 | 0 | 195 | 0 | — |

TABLE 2-continued

| Compound No. | Concentration of the active ingredient (ppm) | Number of mites (*Panonychus ulmi* Koch) | | Number of mites (*Tetranychus urticae* Koch) | | Phytotoxicity |
|---|---|---|---|---|---|---|
| | | Before spraying | 30 days after spraying | Before spraying | 30 days after spraying | |
| | 125 | 198 | 35 | 191 | 156 | — |
| X | 500 | 204 | 0 | 211 | 0 | — |
| | 250 | 197 | 18 | 203 | 96 | — |
| XI | 500 | 193 | 0 | 202 | 0 | — |
| | 250 | 196 | 43 | 213 | 57 | — |
| Not sprayed | — | 198 | 328 | 178 | 411 | — |

TEST EXAMPLE 3

Adults of *Amblyseius longispinosus* Evans (beneficial mite) were released in numbers of 10 per pot to kidney beans (two-leaf stage) growing in pots. Each of the compounds in predetermined concentrations was fully sprayed onto the kidney beans and air dried, and then the kidney beans were cut and placed on kidney beans in pots on which *Tetranychus telarius* Linné was growing so as to spontaneously move the *Amblyseius longispinosus* to the kidney beans. Two days after the spraying, the mortality of the *Amblyseius longispinosus* was examined. As comparative chemicals, bis(tri-n-pentyltin) oxide, tributyltin chloride and tri(2-ethylbutyl)tin chloride were similarly formulated and sprayed in the same way as above. The results are shown in Table 3.

TABLE 3

| Compound No. | Concentration of the active ingredient (ppm) | Number of mites tested | Death rate after 2 days (%) |
|---|---|---|---|
| III | 500 | 30 | 0 |
| IV | 500 | 30 | 0 |
| VI | 500 | 30 | 0 |
| VII | 500 | 30 | 5 |
| IX | 500 | 30 | 0 |
| Comparison A | 500 | 30 | 67 |
| Comparison C | 500 | 30 | 100 |
| Comparison F | 500 | 30 | 100 |
| Not sprayed | — | 30 | 0 |

Note:
Comparison A: bis(tri-n-pentyltin) oxide
Comparison C: tributyltin chloride
Comparison F: tri(2-ethylbutyl)tin chloride

TEST EXAMPLE 4

The following chemicals in th concentrations indicated were each sprayed fully by a sprayer for chromatography using kidney beans without a climbing stem (two-leaf stage) and Tokinashi radish (three-leaf stage) grown in pots as test plants. The sprayed chemicals were dried in the air, and then the pots were placed in a greenhouse. One week after the spraying, the plants were examined, and the degree of phytotoxicity was evaluated on the following scale.

| | |
|---|---|
| + + + + +: | Enormous (withered) |
| + + + +: | Great |
| + + +: | Medium |
| + +: | Small |
| +: | Slight |
| —: | None (no effect) |

The results are shown in Table 4.

TABLE 4

| Compound No. | Concentration of the active ingredient (ppm) | Degree of phytotoxicity Kidney beans | Radish |
|---|---|---|---|
| I | 2000 | — | — |
| II | 2000 | — | — |
| III | 2000 | — | — |
| IV | 2000 | — | — |
| V | 2000 | — | — |
| VI | 2000 | — | — |
| VII | 2000 | — | — |
| IX | 2000 | — | — |
| XI | 2000 | — | — |
| Comparison A | 2000 | + | + |
| Comparison B | 2000 | + | ++ |
| Comparison C | 2000 | +++++ | ++++ |
| Comparison D | 2000 | + | + |
| Comparison G | 2000 | +++ | +++ |
| Not sprayed | — | — | — |

Note:
Comparison A: bis(tri-n-pentyltin) oxide
Comparison B: tricyclohexyltin hydroxide
Comparison C: tributyltin chloride
Comparison D: bis(tri-n-heptyltin) oxide
Comparison G: bis(tri-2-hexyltin) oxide

What we claim is:

1. An horticultural composition for controlling plant mites comprising
   (1) a nonphytotoxic horticulturally acceptable carrier, and
   (2) as an essential active ingredient, a miticidally effective amount of a nonphytotoxic trialkyltin compound of the formula:

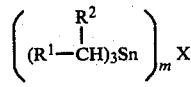

wherein $R^1$ represents a linear alkyl group having 6 to 11 carbon atoms, $R^2$ represents a hydrogen atom or a methyl group, provided that the sum of the number of carbon atoms of $R^1$ and $R^2$ is from 7 to 11, m is an integer of 1 or 2, and X is selected from the group consisting of chlorine, fluorine, hydroxyl, acetoxy, dithiocarbamate, laurylmercapto, when m is 1; and a member selected from the group consisting of oxygen, sulfur, and sulfate when m is 2, said trialkyltin tin compound being present in the composition in an amount of from about 20 to 3000 ppm.

2. The composition of claim 1 wherein X in the formula is a chlorine atom or a hydroxyl group.

3. The composition of claim 1 wherein X in the formula is an oxygen atom.

4. The composition of claim 1 wherein the carrier is a liquid.

5. The composition of claim 1 wherein the carrier is water.

6. The composition of claim 1 which is in the form of a concentrate capable of being diluted with an additional carrier before application.

7. The composition of claim 6 wherein the concentration of the trialkyltin compound is 1 to 80% based on the weight of the composition.

8. A method for controlling plant mites, which comprises applying to said mites or to their habitat a composition comprising (1) a carrier and (2) an miticidally effective amount of a nonphytotoxic trialkyltin compound of the formula:

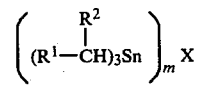

wherein $R^1$ represents a linear alkyl group having 6 to 11 carbon atoms, $R^2$ represents a hydrogen atom or a methyl group, provided that the sum of the number of carbon atoms of $R^1$ and $R^2$ is from 7 to 11, m is an integer of 1 or 2, and X is selected from the group consisting of chlorine, fluorine, hydroxyl, acetoxy dithiocarbamate, laurylmercapto when m is 1; and a member selected from the group consisting of oxygen, sulfur, and sulfate when m is 2.

9. The method of claim 8 wherein said composition is applied to the plants in an amount of about 0.09 to about 3.5 kg of th trialkyltin compound per hectare.

10. The method of claim 8 wherein X in the formula is a chlorine atom or a hydroxyl group.

11. The method of claim 8 wherein X in the formula is an oxygen atom.

12. A method according to claim 8, wherein said composition is applied in an amount of about 0.22 to 2.3 kg. of the trialkyl tin compound per hectare.

* * * * *